(12) United States Patent
Presthus et al.

(10) Patent No.: US 9,539,079 B2
(45) Date of Patent: Jan. 10, 2017

(54) SYSTEMS, METHODS, AND IMPLANTS FOR TREATING PROLAPSE OR INCONTINENCE

(76) Inventors: James B. Presthus, Edina, MN (US); Emily R. Rolfes Meyering, Eden Prairie, MN (US)

( * ) Notice: Subject to any disclaimer, the term of this patent is extended or adjusted under 35 U.S.C. 154(b) by 158 days.

(21) Appl. No.: 14/236,425

(22) PCT Filed: Aug. 3, 2012
(Under 37 CFR 1.47)

(86) PCT No.: PCT/US2012/049577
§ 371 (c)(1),
(2), (4) Date: Jun. 4, 2014

(87) PCT Pub. No.: WO2013/020076
PCT Pub. Date: Feb. 7, 2013

(65) Prior Publication Data
US 2015/0018602 A1    Jan. 15, 2015

Related U.S. Application Data

(60) Provisional application No. 61/514,665, filed on Aug. 3, 2011.

(51) Int. Cl.
*A61F 2/00* (2006.01)

(52) U.S. Cl.
CPC ...... *A61F 2/0045* (2013.01); *A61F 2210/0057* (2013.01); *A61F 2250/0007* (2013.01)

(58) Field of Classification Search
CPC ............ A61B 2017/00805; A61F 2210/0057; A61F 2250/0007; A61F 2/0045; A61F 2/0004;A61F 2/0009; A61F 2/0036–2/00451
See application file for complete search history.

(56) References Cited

U.S. PATENT DOCUMENTS

| | | |
|---|---|---|
| 4,911,165 A | 3/1990 | Lennard et al. |
| 5,112,344 A | 5/1992 | Petros |
| 5,611,515 A | 3/1997 | Benderev et al. |
| 5,842,478 A | 12/1998 | Benderev et al. |

(Continued)

FOREIGN PATENT DOCUMENTS

| | | |
|---|---|---|
| WO | WO 03/096929 | 11/2003 |
| WO | 2005/094694 A2 | 10/2005 |

(Continued)

OTHER PUBLICATIONS

Organ, S.J., "Phase separation in blends of poly(hydroxybutrate) with poly(hydroxybutrate-co-hydroxyvalerate): variation with blend components" Polymer, vol. 35, No. 1, pp. 86-92, 1994.

(Continued)

*Primary Examiner* — John Lacyk
(74) *Attorney, Agent, or Firm* — Kagan Binder, PLLC

(57) ABSTRACT

Described are pelvic implants, systems including the implant and a delivery tool, and methods for the treatment of incontinence or prolapse. The implant has an expansion member associated with a support portion and a tensioning member along an extension portion of the implant. Systems and methods for treating incontinence or prolapse that include a composition having non-absorbable fibers of different sizes that can be applied to and set on an implant are also provided.

24 Claims, 8 Drawing Sheets

(56) References Cited

U.S. PATENT DOCUMENTS

| | | | |
|---|---|---|---|
| 5,860,425 A | 1/1999 | Benderev et al. | |
| 5,899,909 A | 5/1999 | Claren et al. | |
| 6,039,686 A | 3/2000 | Kovac | |
| 6,042,534 A | 3/2000 | Gellman et al. | |
| 6,110,101 A | 8/2000 | Tihon et al. | |
| 6,382,214 B1 | 5/2002 | Raz et al. | |
| 6,494,887 B1* | 12/2002 | Kaladelfos | A61B 17/0469 606/119 |
| 6,641,524 B2 | 11/2003 | Kovac | |
| 6,648,921 B2* | 11/2003 | Anderson | A61F 2/0045 600/37 |
| 6,652,450 B2 | 11/2003 | Neisz et al. | |
| 6,702,827 B1* | 3/2004 | Lund | A61B 17/1227 600/29 |
| 6,911,003 B2 | 6/2005 | Anderson et al. | |
| 7,070,556 B2 | 7/2006 | Anderson et al. | |
| 7,351,197 B2 | 4/2008 | Montpetit et al. | |
| 7,407,480 B2 | 8/2008 | Staskin et al. | |
| 7,422,557 B2 | 9/2008 | Arnal et al. | |
| 7,500,945 B2 | 3/2009 | Cox et al. | |
| 7,722,528 B2 | 5/2010 | Arnal et al. | |
| 7,740,576 B2 | 6/2010 | Hodroff et al. | |
| 7,901,346 B2 | 3/2011 | Kovac et al. | |
| 7,905,825 B2 | 3/2011 | Arnal et al. | |
| 7,914,437 B2 | 3/2011 | Gozzi et al. | |
| 2001/0029398 A1 | 10/2001 | Jadhav | |
| 2002/0188342 A1 | 12/2002 | Rykhus, Jr. et al. | |
| 2004/0039453 A1 | 2/2004 | Anderson et al. | |
| 2004/0087970 A1 | 5/2004 | Chu et al. | |
| 2005/0043580 A1 | 2/2005 | Watschke et al. | |
| 2005/0065395 A1 | 3/2005 | Mellier | |
| 2005/0234291 A1* | 10/2005 | Gingras | A61F 2/0045 600/30 |
| 2006/0058574 A1* | 3/2006 | Priewe | A61B 1/00087 600/29 |
| 2006/0142794 A1* | 6/2006 | Lendlein | A61F 2/04 606/191 |
| 2006/0195007 A1 | 8/2006 | Anderson et al. | |
| 2006/0195011 A1* | 8/2006 | Arnal | A61B 17/06066 600/37 |
| 2006/0260618 A1 | 11/2006 | Hodroff et al. | |
| 2007/0088189 A1 | 4/2007 | Levy | |
| 2008/0200751 A1* | 8/2008 | Browning | A61B 17/0401 600/30 |
| 2008/0269547 A1* | 10/2008 | Hortenstine | A61F 2/0045 600/30 |
| 2008/0269548 A1 | 10/2008 | Vecchiotti et al. | |
| 2009/0137864 A1 | 5/2009 | Cox et al. | |
| 2009/0259092 A1* | 10/2009 | Ogdahl | A61F 2/0045 600/30 |
| 2009/0306464 A1 | 12/2009 | Griguol | |
| 2010/0191045 A1 | 7/2010 | Gobron et al. | |

FOREIGN PATENT DOCUMENTS

| | | | |
|---|---|---|---|
| WO | WO 2007/016083 | 2/2007 | |
| WO | WO 2007/097994 | 8/2007 | |
| WO | 2007/149348 A2 | 12/2007 | |
| WO | WO 2010/027796 A1 * | 3/2010 | A61F 2/0045 |
| WO | WO 2011/063412 | 5/2011 | |
| WO | WO 2011/072148 | 6/2011 | |

OTHER PUBLICATIONS

Gassner, et al., "Physical properties of PHB-PCL" Polymer, vol. 35, No. 10, pp. 2233-2236, 1994.

Gurav et al., "A qualitative in vitro evaluation of the degradable materials poly(caprolactone), poly(hydroxybutrate) and a poly(hydroxybutrate)-hydroxyvalerate) copolymer" Journal of Materials Science: Materials in Medicine 5, pp. 784-787, 1994.

Stamey, "Endoscopic Suspension of the Vesical Neck for Urinary Incontinence in Females" Ann. Surgery, pp. 465-471, Oct. 1980.

Pereyra, "A Simplified Surgical Procedure for the Correction of Stress Incontinence in Women" West. J. Surg., Obstetrics & Gynecology, pp. 243-246, Jul.-Aug. 1959.

* cited by examiner

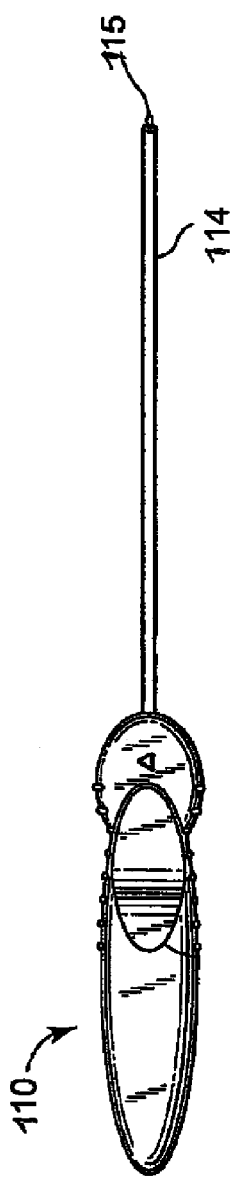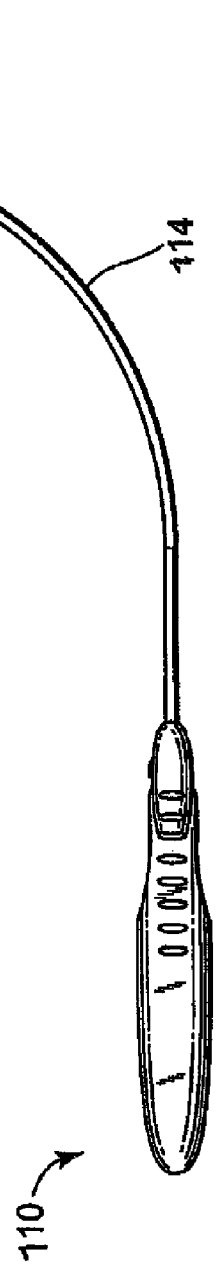
Fig. 8
Fig. 9

SYSTEMS, METHODS, AND IMPLANTS FOR TREATING PROLAPSE OR INCONTINENCE

PRIORITY CLAIM

This application claims the benefit from International No PCT/US2012/049577, which was granted an International filing date of Aug. 3, 2012, which in turns claims priority to U.S. Provisional Patent Application Ser. No. 61/514,665, filed on Aug. 3, 2011, titled Ideas for Incontinence-Prolapse Treatment, which applications are hereby incorporated by reference in their entireties.

FIELD OF THE INVENTION

The invention relates to systems, implants, and methods for treating female pelvic conditions such as female urinary incontinence and vaginal prolapse conditions such as enterocele, rectocele, cystocele, and vault prolapse. The systems, implants, and methods include a pelvic implant to support pelvic tissue with one or more of a tensioning member, an expandable support portion, and/or a fiber-containing composition for application to the implant.

BACKGROUND

Pelvic health for women is a medical area of increasing importance, at least in part due to an aging population. Examples of common pelvic ailments include incontinence and pelvic tissue prolapse. Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as uterine and vaginal vault prolapse. A cystocele is a hernia of the bladder, usually into the vagina and introitus. Pelvic disorders such as these can result from weakness or damage to normal pelvic support systems.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Female stress urinary incontinence (SUI) occurs when the patient is physically stressed.

The female's natural support system for the urethra is a hammock-like supportive layer composed of endopelvic fascia, the anterior vaginal wall, and the arcus tendineus. Weakening and elongation of the pubourethral ligaments and the arcus tendineus fascia pelvis, and weakening of the endopelvic fascia and pubourethral prolapse of the anterior vaginal wall, may have a role in the loss of pelvic support for the urethra and a low non-anatomic position that leads to urinary incontinence.

In general, urinary continence is considered to be a function of urethral support and coaptation. For coaptation to successfully prevent or cure incontinence, the urethra must be supported and stabilized in its normal anatomic position. A number of surgical procedures and implantable medical devices have been developed over the years to provide urethral support and restore coaptation. Examples of such surgical instruments included Stamey needles, Raz needles, and Pereyra needles. See Stamey, Endoscopic Suspension of the Vesical Neck for Urinary Incontinence in Females, Ann. Surgery, pp. 465-471, October 1980; and Pereyra, A Simplified Surgical Procedure for the Correction of Stress Incontinence in Women, West. J. Surg., Obstetrics & Gynecology, pp. 243-246, July-August 1959.

One alternative surgical procedure is a pubovaginal sling procedure. A pubovaginal sling procedure is a surgical method involving the placement of a sling to stabilize or support the bladder neck or urethra. There are a variety of different sling procedures. Descriptions of different sling procedures are found in U.S. Pat. Nos. 5,112,344, 5,611,515, 5,842,478, 5,860,425, 5,899,909, 6,039,686, 6,042,534, and 6,110,101.

Some pubovaginal sling procedures extend a sling from the rectus fascia in the abdominal region to a position below the urethra and back again. The slings comprise a central portion that is adapted to support the urethra or a pelvic organ (i.e., a "support portion" or "tissue support portion"), and two extension portions bracketing the support portion, optionally a protective sheath or sheaths encasing at least the extension portions. Although complications associated with sling procedures are infrequent, they do occur. Complications include urethral obstruction, prolonged urinary retention, bladder perforations, damage to surrounding tissue, and sling erosion.

Other treatments involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced to the retropubic space. Peripheral or extension portions of the elongated urethral sling are affixed to bone or body tissue at or near the retropubic space. A central support portion of the elongated urethral sling extends under the urethral or bladder neck to provide a platform that compresses the urethral sphincter, limits urethral distention and pelvic drop, and thereby improves coaptation. Similar attached slings or supports have been proposed for restoring proper positioning of pelvic organs, e.g., the vagina or bladder.

Elongated "self-fixating" slings have also been introduced for implantation in the body, to treat pelvic conditions such as prolapse and incontinence conditions. Self-fixating slings do not require the extension portions to be physically attached to tissue or bone. Rather, the slings rely upon tissue ingrowth into sling pores to stabilize the sling. See, for example, commonly assigned U.S. Pat. Nos. 6,382,214, 6,641,524, 6,652,450, and 6,911,003, and publications and patents cited therein. The implantation of these implants involves the use of right and left hand sling implantation tools that create transvaginal, transobturator, supra-pubic, or retro-pubic exposures or pathways. A delivery system for coupling the sling ends to ends of elongate insertion tools, to draw sling extension portions through tissue pathways, is also included. Needles of the right and left hand insertion tools described in the above-referenced 2005/0043580 patent publication have a curvature in a single plane and correspond more generally to the BioArc™ SP and SPARC™ single use sling implantation tools sold in a kit with an elongated urethral sling by American Medical Systems, Inc.

In some sling implantation kits, the needle portion has a proximal straight portion extending from the handle and a distal curved portion terminating in a needle end or tip. As described in the above-referenced '003 patent, the kit may include more than one type of implantation tool (also, "insertion tool"). The kit may include one tool suitable for an outside-in (e.g. from the skin incision toward a vaginal incision) procedure and another that may be suitable for an inside-out (e.g. from the vaginal incision toward a skin incision) procedure. Surgeons that prefer an approach dictated by the surgeon's dominant hand can select the procedure and the appropriate implantation tool. Alternately, universal implantation tools (e.g., right and left sling implantation tools each suitable for both an inside-out and an outside-in approach) may be provided.

Optionally, a detachable protective sheath may encase some portion of an extension portion of a pelvic implant. Connectors (e.g., dilating connectors) may be attached to the ends of the extension portions for connecting with and end of an insertion tool. Generally speaking, the insertion tool ends are inserted axially into the connectors and the extension portions of the implant are drawn through tissue pathways trailing the connector and needle, to draw a central support portion against the pelvic tissue (e.g., the urethra) to provide support. The connectors are drawn out through skin incisions and the implant and sheath are severed adjacent to the connectors.

Similar transobturator implantation procedures for implanting a pelvic implant to support a pelvic organ, e.g., the vagina, restored in proper anatomic position, are described in commonly assigned U.S. Patent Application Publication Nos. 2005/0043580 and 2005/0065395. Alternate implantation procedures for creating tissue pathways exiting the skin lateral to the anus and implanting an implant extending between the skin incisions to support a pelvic organ, e.g., the vagina, restored in proper anatomic position, are described in commonly assigned U.S. Patent Application Publication No. 2004/0039453 and in PCT Publication No. WO 03/096929. Various ways of attaching a sheath end and implant mesh extension to a self-fixating tip are detailed in the above-referenced '450 patent, for example. Further ways of attaching extensions of an implant to an implantation tool are described in U.S. Patent Publication 2004/0087970.

SUMMARY

The present application describes systems, implants, and methods for treating female pelvic conditions such as female urinary incontinence and vaginal prolapse. The application describes implants having improved adjustability and stability following implantation. The application also describes implants having improved patient conformability and strength.

In one embodiment, the invention provides an implant configured for transvaginal insertion and to provide support to the urethra. The implant comprises a central support portion and one or more extension portion(s) from the central support portion. The central support portion comprises an expansion member configured to expand in contact with periurethral tissue. The implant further comprises a tensioning member positioned along the extension portion. The extension portion can be adjusted in conjunction with the tensioning member to provide tensioning of the implant following implantation.

In a related embodiment, the invention provides systems for the treatment of incontinence or prolapse. The system comprises an implant and an implant delivery tool. The implant comprises a central support portion and one or more extension portion(s) from the central support portion. The central support portion comprises an expansion member configured to expand in contact with periurethral tissue. The implant further comprises a tensioning member positioned along the extension portion. The extension portion can be adjusted in conjunction with the tensioning member to provide tensioning of the implant following implantation. The delivery tool is configured to transvaginally deliver the implant and position the support portion of the implant in contact with periurethral tissue. In some embodiments the delivery tool comprises a hollow portion or bore in which a portion or all of the implant can be placed. In some embodiments at least a portion of the implant is loaded in the implant delivery tool to provide the expansion member in a compressed configuration.

In a related embodiment, the invention provides a method for the treatment of incontinence or prolapse. The method comprises steps of: (a) providing a system comprising an implant associated with an implant delivery tool, wherein the implant is configured for transvaginal insertion and to provide support to the urethra, the implant central support portion and one or more extension portion(s) from the central support portion, wherein the central support portion comprises an expansion member, the implant further comprising a tensioning member positioned along the extension portion, (b) delivering the implant transvaginally into pelvic tissue to place the central support portion in contact with periurethral tissue; (c) allowing expansion member to expand in contact with periurethral tissue; and (d) adjusting the extension portion using the tensioning member to provide tensioning of the implant to provide treatment of incontinence or prolapse.

The implants having the expansion member and the tensioning member provide better stability and positioning of the implant following surgical placement. This can lead to a better clinical outcome as the support portion is less likely move from its initial position in association with the periurethral tissue.

In other embodiments, the invention provides a system and method that uses a fiber-containing composition to form a reinforced implant.

For example, in one embodiment the invention provides a system for the treatment of anterior or posterior vaginal repair, the system comprising: (a) an implant for the treatment of anterior or posterior vaginal repair; and (b) a composition comprising non-absorbable fibers of different sizes which can be applied to and set on all or a portion of the implant.

In a related embodiment, the invention provides a method for promoting anterior or posterior vaginal repair. The method comprises steps of: (a) providing an implant for the treatment of anterior or posterior vaginal repair; (b) applying a composition comprising non-absorbable fibers of different sizes to all or a portion of the implant to form a reinforced implant; and (c) providing the reinforced implant at a pelvic tissue location to promote anterior or posterior vaginal repair.

The composition comprising non-absorbable fibers can be applied to the implant prior to, during, or after implantation. The applied fibers can provide an implant that better conforms to the patient's anatomy at the implantation site. The applied fibers can also reinforce the implant to provide additional support strength for treatment of anterior or posterior vaginal repair.

BRIEF DESCRIPTION OF DRAWINGS

FIGS. 8-12 illustrate example embodiments of various insertion tools.

DETAILED DESCRIPTION

Figure 1:
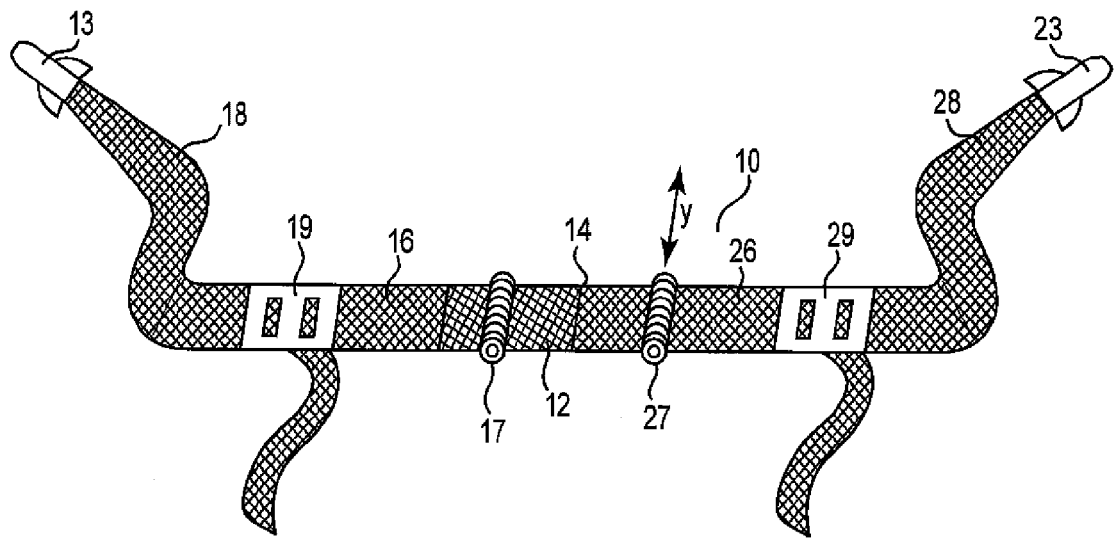
FIG. 1 illustrates a perspective view of an implant having expansion members and tensioning members.

The following description is meant to be illustrative only and not limiting. Other embodiments of this invention will be apparent to those of ordinary skill in the art in view of this description.

As a general matter, the invention relates to systems, implants, and methods for treating female pelvic conditions such as female urinary incontinence and vaginal prolapse conditions such as enterocele, rectocele, cystocele, and vault prolapse. The systems, implants, and methods include a pelvic implant to support pelvic tissue with one or more of a tensioning member, an expansion member, and/or a fiber-containing composition for application to the implant. An implant can be implanted in a female to treat a disorder such as urge incontinence, stress urinary incontinence, mixed incontinence, overflow incontinence, functional incontinence, or a female condition including prolapse (e.g. vaginal or uterine), enteroceles (e.g. of the uterus), rectoceles, cystocele, and anatomic hypermobility, or combinations of two or more of these.

Embodiments of the invention provide implant configured for transvaginal insertion and to provide support to the urethra. An implant can include a central support portion configured to contact periurethral tissue and an expansion member that expands upon implantation of the implant. The implant also includes a tensioning member positioned along an extension portion of the implant. The extension portion can be adjusted in conjunction with the tensioning member to provide tensioning of the implant following implantation.

The implant can include a tissue support portion (also referred to as a "central support portion") that can be used to support pelvic tissue such as the urethra (which includes the bladder neck), bladder, vaginal tissue, etc, by contacting periurethral tissue. The support portion can be placed in contact with periurethral tissue which is tissue around, or associated with, the urethra to provide support the urethra and treat the condition. The expansion member associated with the support portion is expanded in contact with the periurethral tissue and provides improved stabilization and support of the tissue, leading to a better clinical outcome.

The implant has one or more extension portion(s) that are attached to and extend from the central support portion. Types of exemplary implants that can be generally useful as discussed herein can include those previously and currently used in treating pelvic conditions, including those implants referred to as urethral "slings," "strips," "mesh strips," "hammocks," among other terms for pelvic implants modified with the expansion member and the tensioning member. Examples of implants for treating incontinence, e.g., urethral slings, can include a central support portion and two extension portions. An exemplary sling can generally be in the form of an implantable strip having a central support portion and two extension portions, along with the expansion member and the tensioning member.

The one or more extension portions can lead from the support portion positioned in association with periurethral tissue, to or more other secondary pelvic tissue sites to hold the central support portion in a desired position for treatment. The end of an extension portion can be immobilized at the secondary pelvic tissue site to achieve this effect. For example, the end of an extension portion may be tied, sutured, adhered, or anchored to a certain pelvic tissue or anatomical structure. In some arrangements, a tissue fastener can be included at an end of an extension portion, the tissue fastener being designed to attach to tissue in the pelvic region to secure the distal end of the extension portion to the tissue.

One or multiple (e.g., one, two, four, or six) extension portions can extend from a central support portion for attachment to tissue in the pelvic region, such as by extending through a tissue path to an internal attachment point (for attachment by bone anchor, tissue fastener, etc.).

Exemplary dimensions of the implant can be sufficient to allow the central support portion to contact periurethral tissue to be supported, and to allow extension portions to extend from the tissue support portion to a desired anatomical location to allow the extension portion to be secured to or pass through tissue of the pelvic region and support the tissue support portion.

The central support portion can have a desired shape and area and may be described in terms of width and length. The extension portion(s) are generally elongate and can also be described in terms of width and length, with the extension portion length being greater than the width. In some cases the central portion has a width greater than the width of the extension portion(s). In some cases the central portion has a width that is the same as the width of the extension portion(s), and here the implant can resemble a "strip" of material (e.g., mesh) with a portion of the strip near the center of the strip defining the central support portion.

Dimensions of extension portions according to the invention can allow the extension portion to reach between the central support portion placed to support periurethral tissue (at a "proximal" end of the extension portion connected to the central support portion) and a location at which the distal end of the extension portion attaches to pelvic tissue, as desired, according to various installation procedures.

Exemplary implants can be made of materials and may be generally shaped and sized according to previous implants, but modified to include features as described herein, such as a tensioning member and central support portion with an expansion member, etc. For example an implant can have features as described in the following exemplary documents: U.S. Pat. No. 7,500,945, issued Mar. 10, 2009 (Cox et al.); U.S. Pat. No. 7,070,556, issued Jul. 4, 2006, (Anderson et al.); U.S. Pat. No. 7,905,825, issued Mar. 15, 2011 (Arnal et al.); U.S. Pat. No. 7,722,528, issued May 25, 2010 (Arnal et al.); U.S. Pat. No. 7,422,557, issued Sep. 9, 2008 (Arnal et al.); U.S. Pat. No. 7,914,437, issued Mar. 29, 2011 (Gozzi et al.); United States publication number 2006/0195007, published Aug. 31, 2006 (Anderson et al.); U.S. Pat. No. 7,740,576, issued Jun. 22, 2010 (Hodroff et al.); U.S. Pat. No. 7,901,346, issued Mar. 8, 2011 (Kovac et al.); U.S. Pat. No. 7,351,197, issued. Apr. 1, 2008 (Montpetit et al.); and international publication number WO/2007/016083, published Feb. 8, 2007 (Davila et al.); the entireties of each of these disclosures being incorporated herein by reference.

Exemplary implants can be made of materials and exhibit general size and shape features that might be similar to those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, and Monarc® for treating urinary incontinence.

An implant can include portions (e.g., central support with expandable feature, extension portion(s), tensioning member, anchoring member, etc.) made from synthetic or natural materials. The synthetic or natural materials can form structures of the implant that are biodegradable (also referred to "absorbable" or "degradable") or biostable (also referred to "non-absorbable" or "non-degradable" or "non-biodegradable") following implantation into the pelvic region. Combinations of biostable and biodegradable material can be used to form the implant or specific portions of the implant.

Exemplary biostable materials that can be used to form a portion or portions of the implant include synthetic polymers such as polyamides (e.g., nylons such as polyhexamethylene adipamide and polyhexamethylene sebacamide), PEBAX®, fluoropolymers (e.g., polytetrafluoroethylene (PTFE) and polyvinylidene fluoride (PVF)), polyolefins (e.g. polypropylene and polyethylene), and polyesters such as polyethylene terephthalate (PET), polyvinylchloride (PVC), polyethersulfone (PES), polyurethane (PU), polyetherimide (PEI), polycarbonate (PC), and polyetheretherketone (PEEK).

Combinations of biostable polymeric materials can be used to form the implant. The implant may also be fabricated from one biostable polymeric material in one portion, and a different biostable polymeric material in another portion. Portions of the implant can be formed by molding and extrusion using heat to melt the biostable polymeric material (thermoplastics).

Exemplary biodegradable materials that can be used to form a portion or portions of the implant include synthetic polymers such as polyhydroxyalkanoates, such as poly-4-hydroxybutyrate (P4HB), poly(3-hydroxyvalerate), polylactic acid, poly(lactide-co-glycolide), polycaprolactone, polyphosphazine, polyorthoesters, polyalkeneanhydrides, polyanhydrides, and polyesters, and the like.

Polyhydroxyalkanoates include homopolymers such as poly-4-hydroxybutyrate (P4HB), poly(3-hydroxyvalerate), and hydroxyalkanoate copolymers such as poly(hydroxybutyrate-co-hydroxyvalerate) (Organ, S. J. (1994) Polymer, 35, 1:86-92) Blends of hydroxyalkanoate polymers with other absorbable polymers have also been prepared, such as poly(β-hydroxybutyrate) and poly(ε-caprolactone) blends (Gassner, F., and Owen, A. J. (1994) Polymer, 35, 10:2233-2236).

Other exemplary materials that can be used to form the implant are natural materials, such as tissue derived from an animal source, or natural polymeric materials obtained from an organism (e.g., animal, plant, or microorganism). Exemplary tissues derived from animal sources include collagenous tissues (e.g., tissue grafts). The collagenous tissue can be processed such as by mechanical or chemical cleaning, or both which can remove cellular debris from the tissue preparation. The processed tissue can provide properties similar to it native structure and strength. Exemplary natural tissues include those from porcine and cadaveric sources.

An implant can include portions (e.g., central support with the expansion member and extension portion(s)) made from woven materials. In some cases, the mesh can be of a "woven" construction made from monofilaments, multifilaments, yarns of polymeric material, or combinations thereof. A woven mesh generally has openings and the size and shape of these openings can be defined by the weave or knitting patterns of the woven mesh. The openings can be of any one or combination of shapes, such as square, rectangular, triangular, oval, circular, or more complex polygonal shapes (hexagonal, etc.), as well as irregular shapes, such as might be associated with more complex knitted or woven constructs.

The central support portion with expansion member and extension portion(s) of the implant can be made from the same woven mesh or from different woven meshes. In some cases the central support portion and the extension portions (s) are of a continuous weave. In other cases the central support portion and the extension portions(s) are not a continuous weave and are stitched together to join these portions of the implant.

In some embodiments the implant portions having a knitted or woven construction using biostable monofilaments, such as polypropylene monofilaments (see, for example, U.S. Pat. No. 4,911,165). In some embodiments the implant portions having a knitted or woven construction using biodegradable monofilaments, such as poly(L-lactide) (PLLA) monofilaments (see, for example, Kinoshita, Y. et al. (1993) Biomaterials; 14:729-36.). Exemplary monofilaments have diameters in the range of about 10 µm to about 250 µm (~0.0004 to ~0.01 inches), or more specifically from about 25 µm to about 150 µm (~0.001 to ~0.006 inches).

Some example of commercially available synthetic materials include MarleX™ (polypropylene) available from Bard of Covington, R.I., Prolene™ (polypropylene) and Mersilene (polyethylene terephthalate) Hernia Mesh available from Ethicon, of New Jersey, Gore-TeX™ (expanded polytetrafluoroethylene) available from W.L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon.

All or portions of the implants of the invention (e.g., including multi-piece implants) can be made from a woven mesh. For example, the central support portion and the one or more extension portions can be made from a woven mesh. Alternatively, one portion of the implant can be made from a woven mesh, and another portion of the implant can be made from a material that is different than the woven mesh, such as a molded, non-woven, mesh, or a naturally derived material, including those described herein.

In other constructions the implant can include portions (e.g., central support with expandable feature and extension portion(s)) having a non-knitted/non-woven (e.g., molded) polymeric mesh layer. Molded polymeric meshes are described in, for example, commonly assigned PCT Publication Nos. WO2011/063412 and WO2011/072148, which describes molded meshes made from biostable polymers such as polypropylene; Use of bioabsorbable polymers such as PGA and PLA are also described as materials for making the molded meshes.

Molded (non-knitted/non-woven) meshes can be formed of patterned cells by way of a molding, die casting, laser etching, laser cutting, extruding, punching, or 3-D printing process. The portion of the implant that is the non-knitted/non-woven mesh can be considered a homogenous unitary construct. The pattern cut or formed implant can be constructed of a non-absorbable polymer material to provide a lattice support structure of repeated apertures or cells. Repeated apertures in the implant generally form a lattice structure and can be cut or molded into sinusoid, or other waveform or undulating strut patterns to control elongation or compression along single or multiple axes to define a desirable pattern density with overall reduced surface area, and to control the distribution and shaping from applied loads.

All or portions of the implants of the invention (e.g., including multi-piece implants) can be made from a molded, non-woven, mesh. For example, the central support portion and one or more extension portions can be made from a molded mesh. Alternatively, one portion of the implant can be made from a molded mesh, and another portion of the implant can be made from a material that is different than the molded, non-woven, mesh, such as a woven material, or a naturally derived material, including those described herein.

A multi-layer tissue support portion can include a layer of naturally derived material that is sized and shaped to contact the periurethral tissue to be supported and can have a synthetic layer (e.g., woven or molded mesh) that is of the same size and shape as the layer of naturally derived material, to produce a central support portion. A central support portion can include, e.g., a synthetic mesh layer and layer of naturally derived material that are identical or substantially-identical in shape and size; the mesh layer may additionally include one or more extension portions that extend beyond the area of the naturally derived material.

Two layers of a multi-layer tissue support portion may be formed and held together as desired, such as by stitching, sutures, staples, adhesive, thermoforming, polymeric rivets, etc. In use, a layer of naturally derived material can be placed adjacent to sensitive tissue such as vaginal tissue, e.g., to prevent tissue erosion.

In some constructions, an expansion member, or an expandable frame including an expansion member, as described herein, is positioned between two layers of a multilayer construct. The multiple layers can optionally be of the same size and shape, similar sizes and shapes, or different sizes and shapes.

The central support portion of the implant can include an expansion member. In some cases, the expansion member can be an elongate rigid element or component that has internal physical properties sufficient to change from a "second" (compressed) configuration to a "first" (expanded) configuration. The first, expanded, configuration may be referred to as the "natural configuration" or "working configuration." The expansion member can be formed from one or more biocompatible materials having a resilient property, or having shape memory properties. A resilient property is reflected by the ability of the member to revert to its natural "first" configuration from, for example, a compressed or constrained "second" configuration, as seen in springs. Shape memory can be affected by changes in temperature of the expansion member.

In some aspects the expansion member is formed from a polymeric material, such as a biostable or biodegradable polymeric material. The expansion member may be made from a biodegradable polymer such as a polyanhydride, polycaprolactone, polyglycolic acid, poly-L-lactic acid, poly-D-L-lactic acid, polyphosphate esters or combinations of these.

Shape memory polymers (SMP) such as AB-polymer networks based upon oligo(e-caprolactone) dimethylacrylates and n-butyl acrylate are also known in the art and can be used to form the expansion member.

The expansion member can also be formed of any medically-acceptable, biocompatible metal, such as MP35N alloy, titanium, stainless steel, Nitinol™, or other similar inert biocompatible metal. Alternatively, the expansion member can be formed of any resilient medically-acceptable, biocompatible plastic such polyvinylchloride (PVC) or polyetheretherketone (PEEK). Shape memory alloys are characterized by a martensite phase (lower tensile strength, stable at low temperatures), and an austenite phase (high tensile strength, stable at temperatures higher than the martensite phase). One preferred shape memory alloy for biomedical applications is Nitinol™.

The expansion member can be of any shape or design so it can exist in first and second configurations. Exemplary shapes and designs include non-linear shapes such as random and regular curved, angled, wave, zig-zag, twisted, coiled, helical, spiral, and undulating shapes. These shapes may include, for example, single or repeating "S"-, "C"-, "V"-, "Z"-, or "J"-patterns.

The expansion member can be in the form of a spring. The spring can have any shape or configuration. For example, in some cases the spring can have a coiled or helical shape. Alternatively the spring can have a flatted shape, such as a flattened wave shape. Other spring forms are flat strip forms and wire forms.

The expansion member can also have a complex shape. For example, the expansion member can be in the form of a braided or fenestrated structure formed from resilient polymeric material. Exemplary forms are those having cylindrical shapes, such as stent configurations, including braided stents made from biocompatible materials. Exemplary bioresorbable, self-expanding stents are described in US Publication No. 2002/0188342 (Rykhus) and 20010029398 (Jadhav), which can be modified and used in association with the central support portion of the implant. Monofilaments made from poly-L-lactide, poly-D-L-lactide or poly-ϵ-caprolactone, or blends thereof, can be formed into monofilaments, and the monofilaments can then be braided into a stent structure.

The support portion can include an expansion member and a woven or nonwoven mesh or other porous construction. In some constructions, the mesh and expansion member(s) are arranged in the support portion so the mesh expands along with the expansion member(s) during implantation. Release of the expansion member(s) from a compressed state can cause its elongation and the mesh can be forced by the expansion member to expand as well.

In some constructions the mesh can be attached to the expansion member at one or more locations. For example, a first position on the mesh (support portion) can be attached to one end of an expansion member, and a second position on the mesh can be attached to the other end of the expansion member.

The first and second positions on the mesh can in some cases correspond to positions along opposite edges of the mesh of the central portion of the implant. Upon release of the expansion member(s) from a compressed state, the mesh will elongate as it is being pulled along via its attachment to the expansion member(s). Points on the mesh can be attached to the expansion member(s) by any suitable method, such as by an adhesive, by melting of points of the mesh to the expansion member(s), or by tying (e.g., suturing) a point of the mesh to the expansion member(s).

In some embodiments the implant comprises at least one expansion member that is in the form of an elongate structure and which is associated with central support portion of the implant in a direction perpendicular to the direction of the implant. For example, the expansion member can have a coil, helical, or cylindrical shape and can be arranged perpendicular to the direction of the central support and extension portions of the implant. In some cases two or more expansion members are arranged parallel to each other in the support portion, each spaced apart from the midline (center) of the central support portion.

FIG. 1 shows one embodiment of an implant 10 having a central support portion 12, the midline of the central support 14, first expansion member 17 (left side), second expansion member 27 (right side), proximal extension portion 16 (left side), tensioning member 19 (left side), distal extension portion 18 (left side), and tissue anchoring member 13. Proximal extension portion 26 (right side), tensioning member 29 (right side), distal extension portion 28 (right side), and tissue anchoring member 23 are also shown.

The first 17 and second 27 expansion members are shown as coil structures, and can be attached to a mesh structure of the central support portion 12 by twisting the coil through the mesh, or by adhering or tying the coil to the mesh. In some cases, the expansion members are in a cylindrical form, such as a braided or woven stent structure.

The first and second expansion members can be compressible in the Y axis so they can be loaded in a bore of an implantation tool. Upon release from the implantation tool the expansion members can expand back out in the Y axis. The first and second expandable members, for example in a coil or spring shape, can also be wound to have a first, smaller, diameter during implant delivery, and then can at least partially unwind to have a second, larger, diameter after the expandable members along with implant have been released from the delivery tool. The at least partial unwinding to provide a larger diameter can be caused by release of the coil from a compressed state, or by a shape memory property of the coil material (e.g., the warming of the coil upon implantation in the body). Upon assuming a greater diameter, greater force is placed upon the periurethral tissue, which stabilizes the central portion of the implant.

In some embodiments, the expandable members have a coil or spring shape and are both compressed in the Y direction, and have a tighter winding (smaller diameter). Upon release of the implant from the insertion tool, the expansion member can elongate in the Y direction, and also expand to a greater diameter.

Figure 2:
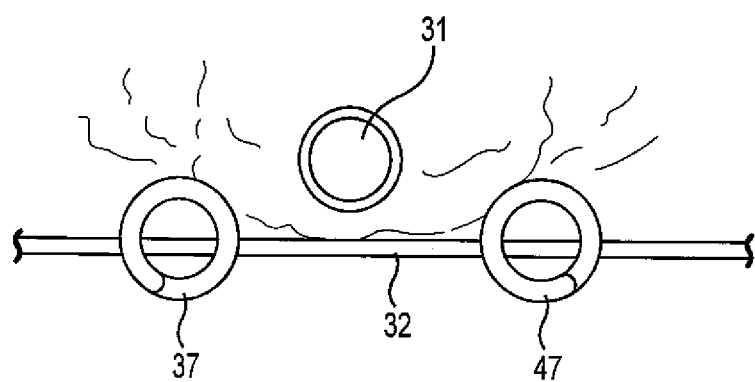
FIG. 2 illustrates a cross-sectional view of an implant having expansion members positioned below the urethra.

As shown in FIG. 2, in an expanded state following release of the implant, the central support portion 32 (e.g., made of a woven or molded mesh) can be underneath the urethra 31, with the first 37 and second 47 expansion members associated with the central support portion and positioned beneath and to the side of the urethra 31. The expanded first and second expansion members are able to exert pressure on the periurethral tissue beneath and to each side of the urethra, thereby providing an improved support structure.

In other constructions the mesh can be in contact with the expansion member, but is not required to be attached to the expansion member at any point. For example, the mesh can partially or completely surround the expansion member, such as being in the form of an envelope or pillow case construction around the mesh. Upon release of the expansion member from a compressed or contracted state, it can apply force to the inside of the mesh structure to force it outwards. Optionally, in this embodiment the mesh can be attached to the expansion member, such as by adhesive or suturing.

In another construction, the central support portion may also include more than one expansion member. The more than one expansion member can be assembled into an "expandable frame" of the central support portion. For example, a plurality of expansion members can be aligned parallel to and spaced from each other over a predetermined distance. If more than one expansion member is used in the central support, the members can be connected by struts to provide a framework. In some constructions, the struts can be arranged parallel to, or substantially parallel to, the expansion members.

The expandable frame can be expandable in one or more directions. In one embodiment, the "expandable frame" is expandable from a second configuration in one direction (e.g., the Y axis), and stationary in another direction (e.g., the X axis). In some cases the X (stationary) axis is parallel, or substantially parallel to, the extension of the extension portions of the implant.

Figure 3:
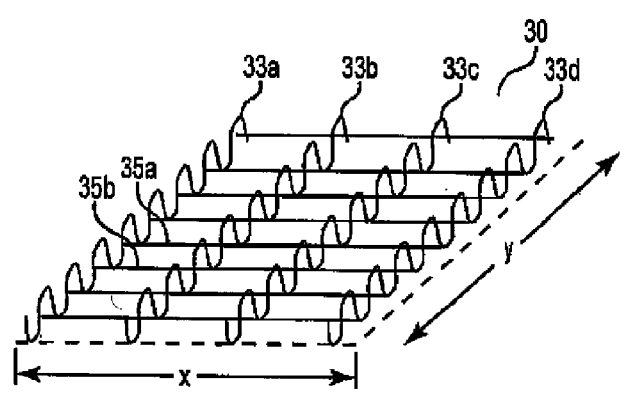
FIG. 3 illustrates an embodiment of an expandable frame having expansion members.
Figure 4:
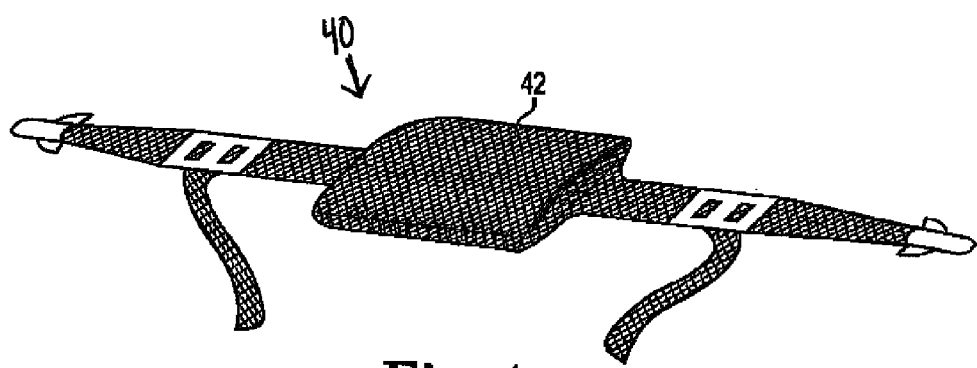
FIG. 4 illustrates a perspective view of an implant having a central support portion including an expanded frame within.
Figure 5:
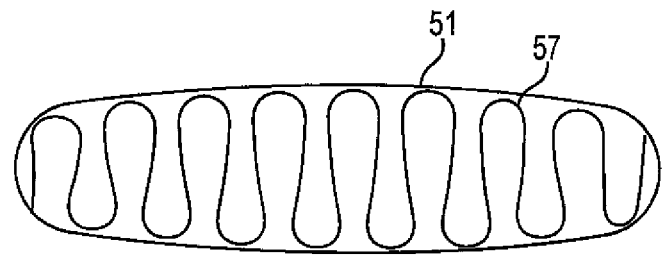
FIG. 5 illustrates an end view of a frame in an expanded configuration, and a mesh structure surrounding the frame.
Figure 6:
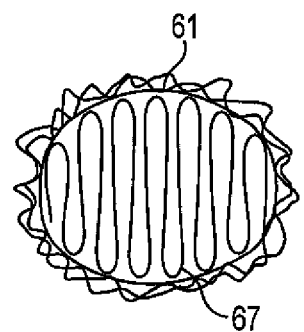
FIG. 6 illustrates an end view of a frame in a compressed configuration, and a mesh structure surrounding the frame.

FIG. 3 shows one embodiment of an expandable frame 30, having spring members 33a, 33b, 33c, and 33d spaced apart and aligned parallel to each other, and compressible in direction Y. The spring members are attached to struts (e.g., 35a and 35b). The frame can be compressed in direction Y and constrained, for example, in a lumen of a delivery tool. FIG. 4 shows an implant 40 having a central support portion 42 (e.g., made of a mesh material) encasing and expanded frame. FIG. 5 shows an end of a frame with a spring expansion member 57 in an expanded configuration, and a mesh structure 51 surrounding the frame. In other constructions, instead of the mesh surrounding the frame, the mesh can be positioned on one side (e.g., top or bottom) of the frame. FIG. 6 shows an end of a frame with a spring expansion member 67 in a compressed configuration (as would exist in the lumen of an insertion tool), and a mesh structure 61 surrounding the compressed frame.

In some constructions, expansion of the expansion members causes the support portion of the implant to expand during or after implantation of the implant at a pelvic tissue target site. The central support portion can demonstrate an increase in size, shape, or both, in association with expansion of the expansion member. An expanded central support portion can provides better immobilization at the periurethral tissue as it can exert pressure on the surrounding tissue and prevent movement of the implant following placement.

The central support portion can be in a compressed or compressed configuration when it is implanted in the body. For example, the support portion can be compressed into a portion of a delivery tool, such as a needle, during surgical implantation of the implant. Following its release from the implant, the support portion expands and exerts pressure with the periurethral tissue.

A distal end of an extension portion can optionally include a tissue fastener that attaches to tissue of the pelvic region. The tissue fastener can be, e.g., a soft tissue anchor, a self-fixating tip, a biologic adhesive, a tissue clamp, opposing male and female connector elements that securely engage when pushed together, or any other device to secure a distal end of an extension portion to tissue of the pelvic region. The implant can also have extension portions that do not include a tissue fastener at a distal end of an extension portion, for example if the distal end is designed to be secured to tissue by other methods (e.g., suturing).

A "self-fixating tip" in general can be a structure connected to a distal end of an extension portion that can be implanted into tissue in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through tissue for implantation. The self-fixating tip may engage the insertion tool at an internal channel of the self-fixating tip, at an external location such as at the base, or at a lateral extension, as desired.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

A self-fixating tip may be of any form that can be inserted to tissue of the pelvic region, and that will thereafter be retained in the tissue. Exemplary self-fixating tips can include one or more lateral extensions that can increase the force required to remove the self-fixating tip from tissue after insertion into the tissue, i.e. the "pullout force." At the same time, the lateral extensions can be designed to exhibit a reduced or relatively low "insertion force," which is the amount of force used to insert the self-fixating tip into tissue. A self-fixating tip is designed to be essentially permanently placed upon insertion into tissue, with the single exception that if absolutely necessary to provide desired placement of the self-fixating tip or an attached implant, the self-fixating tip may be removed by a surgeon during an implantation procedure. The self-fixating tip, and all components of the self-fixating tip, can be of combined form and dimensions to result in these functional features. See, e.g., international publication number WO/2007/097994, published Aug. 30, 2007 (Ogdahl et al.), titled Surgical Articles and Methods for Treating Pelvic Conditions, the entirety of which is incorporated herein by reference.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient.

Alternate embodiments of self-fixating tips do not require and can exclude an internal channel for engaging an insertion tool. These alternate embodiments may be solid, with no internal channel, and may engage an insertion tool, if desired, by any alternate form of engagement, such as, for example, by use of an insertion tool that contacts the self-fixating tip at an external location such as by grasping the base (on a side or at the face of the proximal base end) or by contacting a lateral extension.

Embodiments of self-fixating tips also include one or more lateral extension extending laterally (e.g., radially) from the base, such as from a location between the proximal end and the distal end, from a location at the distal base end, or from a location at the proximal base end.

A self-fixating tip can be connected to an extension portion of an implant in any fashion, directly by any attachment mechanism, or indirectly such as through an attachment structure such as a suture. A connection can be based on a mechanical structure, by adhesive, by a connecting suture, or by an integral connection such as by injection molding or "insert" molding (also, "overmolding") as described U.S. Publication No. 2006/0260618-A1, incorporated herein by reference. According to that description a thermoplastic or thermosetting polymer material can be insert molded or injection molded at an end of a mesh extension portion of an implant, e.g., directly to the mesh. By this method, a molded polymer can form a self-fixating tip at an end of an extension portion. The self-fixating tip can be as described herein, for example, including lateral extensions and an internal channel.

The distal end of an extension portion can be attached to any desired tissue of the pelvic region. To attach an extension portion to tissue, a tissue fastener can be attached at the distal end of the extension portion. During installation of the implant, the tissue fastener can be attached to any desired tissue, for example fibrous tissue such as a muscle (e.g., of the obturator foramen, obturator internus, obturator externus, levator ani, coccygeous, iliococcygeous); ligament such as the sacrospinous ligament or surrounding tissue; tendon such as the arcus tendineus or surrounding tissue; or tissue at or near the ischial spine.

Examples of pelvic tissue targets for anchoring include the arcus tendineus ("white line") (e.g., see WO 2007/016083); a region of the coccyx bone (i.e., a "coccyx region" or a "transcoccyx" tissue path) (e.g., see U.S. Pat. No. 7,740,576); a region of the ischial spine, including tissue of the levator ani muscle (iliococcygeous muscle) and arcus tendineus; or the sacrum (see, e.g., Applicant's U.S. Pat. Nos. 7,901,346; 7,407,480, issued Aug. 5, 2008 (Staskin et al.); and U.S. Pat. No. 7,500,945

Useful tissue paths and anatomy for extension portions of implants that support periurethral tissue including the anterior vaginal tissue, the bladder, bladder neck, urethra, or combinations of these, can include tissue paths as described in U.S. Pat. Nos. 7,351,197; 7,407,480; and 7,070,556, the entireties of which are incorporated herein by reference. Such tissue paths may be to the obturator foramen, pubic bone, rectus fascia, retropubic space (attached internally), through the obturator foramen, or through the rectus fascia.

In embodiments of the invention, a length of an extension portion (extended through any tissue path) can optionally be fixed or adjustable. An adjustable extension portion can allow a surgeon to alter the length of an extension portion before, during, or after implantation.

An adjustable extension portion can include a tensioning member to affect the adjustment. The tensioning member can be used in association with one or more of the extension portions of the implant. In some constructions, the implant has two extensions portions from the central support portion, with one of the extension portions having a tensioning member. In other constructions, the implant has two extensions portions from the central support portion, with each extension portion having a tensioning member.

In some embodiments of the invention, an implant including a tensioning member associated with one or more extension portions of the implant can be in the form of a multi-piece implant. A multi-piece implant can have two or more pieces (e.g., two, three, five, six, etc.) depending on the number of tensioning members used with the multi-piece implant. A multi-piece implant can include a central support portion with one or more full or partial extension portions attached to the central support portion, with at least one of the extension portions being a partial extension portion. The extension portions may optionally be referred to as "support portion piece arms." The partial extension portion is represented by a "proximal extension portion" or "proximal extension part" that is attached to the central support portion but does not fully extend to the distal end of the extension portion.

A second piece in the multi-piece implant is a "distal extension portion" or "distal extension part" that is attached to the proximal extension portion via the tensioning member. The multi-piece implant may be described with the distal end of the proximal extension portion attached to the proximal end of the distal extension portion via the tensioning member. In some constructions the tensioning member is affixed to the distal end of the proximal extension portion, and in other cases the tensioning member is affixed to the proximal end of the distal extension portion.

The tensioning member can be positioned at a desired location along the length of an extension portion. If the tensioning member is affixed to the proximal part of the extension portion it will be a predetermined distance from the support portion. If the tensioning member is affixed to the distal part of the extension portion it will be a predetermined distance from the distal end of the extension portion (e.g., self-fixating tip). In certain implant embodiments the tensioning member can be placed at a location that is closer to a distal end of an extension portion than to a tissue support portion of the implant.

A multi-piece implant can be provided to a practitioner in a system or kit where the pieces of the implant are connected to each other via the tensioning member(s), or can be provided in a system or kit where they are not connected. Accordingly, implantation of the multi-piece implant may be carried out where all or parts of the multi-piece implant are connected to each other, or can be carried out where parts of the multi-piece implant are connected to each other. If the parts are not connected to each other during implantation they may be connected to each other (e.g., the proximal extension portion is connected to the distal extension portion via the tensioning member) after implantation of the parts.

In use, the tensioning member can allow adjustment of the length of the extension portion by allowing movement of material of the proximal extension portion, material of the distal extension portion, or both, through the tensioning member. Movement of material through the tensioning member can affect the overall length of the extension portion between its distal end and the central support portion. Movement of extension portion material can also affect the tension between the two when the implant is placed in a patient and the distal end is affixed to a pelvic tissue location, such as the obturator foramen.

In some embodiments, the tensioning member is a "buckle"-type component. Material from the proximal extension portion, distal extension portion, or both, can be led through openings in the buckle. The buckle can act as a frictional element to prevent movement of extension portion material when it has been adjusted to a desired length, such as during or after implantation of the implant. For example, a segment or segments of the extension portion(s) can be frictionally secured by looping a segment of the extension portion through the buckle. That is, an end of an extension portion can be moved through an entry aperture of the buckle around a partitioning element of the buckle, and then out an exit aperture of the buckle.

In some cases the buckle can have a single entry and single exit aperture, such as when either the distal end of the proximal extension portion is affixed to the buckle (so that is provides entry and exit apertures for the proximal end of the distal extension portion), or if the proximal end of the distal extension portion is affixed to the buckle (so that is provides entry and exit apertures for the distal end of the proximal extension portion). In these cases excess material from either the distal end of the proximal extension, or proximal end of the distal extension portion, can be pulled through the exit aperture for adjustment or tensioning of the implant.

In other cases the buckle can have a two pairs of entry and exit apertures to provide entry and exit apertures for the proximal end of the distal extension portion, as well as the distal end of the proximal extension portion. Material from both the distal end of the proximal extension and the proximal end of the distal extension portion can be pulled through the exit aperture for adjustment or tensioning of the implant.

The tensioning member can optionally include teeth, jaws, or other opposing frictional surfaces to allow one-way or two-way movement of material of the extension portion (s), or to prevent movement in one direction or two directions.

Figure 7:
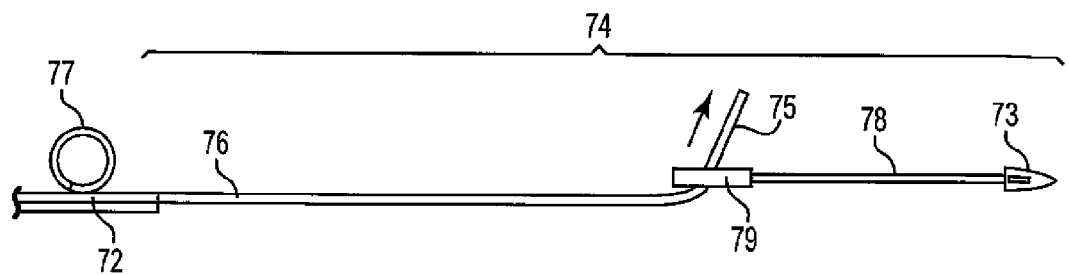
FIG. 7 illustrates a side view of a portion of an implant having an expandable member and a tensioning member.

Exemplary configurations of implants having a central support portion, and extension portion, and a tensioning member are shown in the figures. For example, FIG. 7 shows a portion (right side) of an exemplary implant having an extension portion length 74, tensioning member 79 that is affixed to the proximal end of the distal portion 78 of the extension portion, proximal portion 76 of the extension portion, tissue anchoring member 73, support portion 72, and expansion member 77. The length of extension portion can be adjusted in one direction (shortened) by pulling end 75 through tensioning member 79 in the direction of the arrow.

Implants of the invention, such as those having one or two extension portions, can be used to treat posterior vaginal prolapse such as vaginal vault prolapse, enterocele, rectocele, etc. The extension portions can be attached at an angle to longitudinal axis of central support portion the angle (a) being in the range from 30 to 60 degrees, e.g., from 35 and 55 degrees, or from 40 to 50 degrees, as measured from a line defining the longitudinal axis of tissue support portion and a length-wise axis of an extension portion, while the implant lies flat. Each extension portion can optionally include a tissue fastener attached to the extension portions' distal end. Such an implant can be similar to the Apogee® prolapse product sold commercially by American Medical Systems, Inc.

Implants of the invention, such as those having four extension portions, can be used to treat anterior vaginal prolapse and optionally urinary incontinence. Such an implant can include a central support portion and four extension portions: two superior extension portions and two inferior extension portions. One or more extension portions can include a tensioning member. Such an implant can be similar to the Perigee® prolapse product sold commercially by American Medical Systems, Inc. Tissue fasteners can be present at the end of inferior extension portions and can be placed at a desired pelvic target (e.g., in the region of: ischial spine; sacrospinous ligament, arcus tendineus, obturator foramen, etc.). Distal ends of superior extension portions can be placed, for example, laterally towards or at the obturator foramen.

Optionally, additional extension portions can be added to an implant with four extension portions to make, e.g., an implant with six extension portions, which may be useful for treating prolapse such as anterior prolapse. An exemplary implant with six extension portions can include: two superior extension portions, two inferior extension portions, and two additional extension portions.

An insertion tool can be used to install the implant. Various types of insertion tools are known, and these types of tools and modifications thereof can be used according to this description to install an implant. Examples of useful tools include those types of tool that generally include a thin elongate shaft (e.g., needle) that attaches to a handle; a handle attached to one end (a proximal end) of the shaft; and an optional distal end (or "end tip") of the shaft adapted to engage an end of an extension portion, e.g., a self-fixating tip. The needle can facilitate placement of the distal end of the extension portion at a desired anatomical location that may be internal through a tissue path.

Exemplary insertion tools for treatment of incontinence and vaginal prolapse are described, e.g., in PCT application number 2006/0260618 U.S. Pat. Nos. 7,500,945; 7,070,556; 7,422,557; 7,740,576; and 7,351,197; and PCT publication number WO/2007/016083; each of which is incorporated herein by reference. Tools described in these patent documents are designed for placement of an implant in a pelvic region for the treatment of prolapse or female incontinence, etc. The tools may be curved in two or three dimensions, and may include, for example, a helical portion in three dimensions for placing an extension portion of an implant through a tissue path that passes from a region of the urethra and to an obturator foramen.

Exemplary insertion tools can be similar to or can include features of tools described in the above-referenced patent documents. For use according to certain methods described herein, those insertion tools may be modified, such as to allow the insertion tool to be used to place a self-fixating tip at tissue within the pelvic region through a tissue path that does not extend to an external incision. The insertion tool can be designed, shaped, and sized, to include an elongate shaft that may be straight or that may be curved in two or three dimensions, that can be inserted through a vaginal incision, and extend from that incision to or through pelvic tissue for placement of a distal end of an extension portion.

In some embodiments, the insertion tool comprises a hollow portion (e.g., bore) in which all or a portion of the implants can be placed. The support portion of the implant including one or more expansion member(s) can be housed within a hollow portion of the insertion tool during delivery of the implant to a target location. In some cases the expansion member is in a compressed state in the hollow portion of the insertion tool and then expands upon release (of the support portion) of the implant from the insertion tool. In addition, the insertion tool with a hollow portion can be used to reduce contact between implant and tissue, during implantation. Exemplary insertion tools with hollow portions are described in PCT publication No. WO2007/097994 (see, for example, FIGS. 10-14), and the insertion tools described therein can be modified to provide delivery of implants of the present invention.

The insertion tool can include an elongate tube extending from a handle to the distal end of the tool. Internal bore extends the length of tube to form a hollow interior of tube. The tool may optionally include a slot running along the length of the tube. In some cases, the slot may be used for loading and release of the implant. A portion of an implant can be inserted into slot, to be contained by tube within bore, for implantation. The tube can act to encapsulate or otherwise protect one or more portions of the implant as it is pushed through tissue. The distal end of the insertion tool may be open, closed, or sized to receive a self-fixating tip. For example, the distal end can engage a self-fixating tip by contacting a complementary surface, optionally in a desired orientation. Once an implant is pushed into tissue of the patient using the insertion tool, the implant can be removed from tool by exiting the tube through the slot, or from an opening at the distal end of the tool. The insertion tool can be straight, or curved as desired to reach a desired tissue location.

FIGS. 8 and 9 show a needle 114 and handle 110 suitable for use in the present invention. The handle 110 can be any suitable handle known in the art. The needle 114 is generally curved or arcuate. Overall, the shape of the needle 114 should facilitate and provide controlled passage of the needle 114 through tissue as required. The ends or tip of the needle 114 are generally not sharpened, but may be tapered to afford easy passage through tissue while providing a blunt surface that avoids cutting sensitive tissue such as the bowel. It is preferred that the diameter of the needle 114 be small relative to the prior art to reduce tissue trauma.

The needle 114 is made of a malleable, yet durable, biocompatable surgical instrument materials such as, but not limited to, stainless steel, titanium, Nitinol, polymers, plastics and other materials, including combinations of materials. The needle 114 should have sufficient structural integrity to withstand the various forces (e.g. forces caused by dilator attachment, cystoscopy aid passage, and penetration/passage of the needle 114 through the various tissues) without undergoing any significant structural deformation. Optionally, the needles 114 could be sufficiently malleable to allow a practitioner or user of the device to modify the needle 114 to a desired shape and, thereby, optimize the procedural approach. FIG. 8 shows a needle tip 115. The needle tip is optionally adapted to connect securely to a connector on the end of a sheath associated with at least one of the end portions of the support member.

Figure 10:
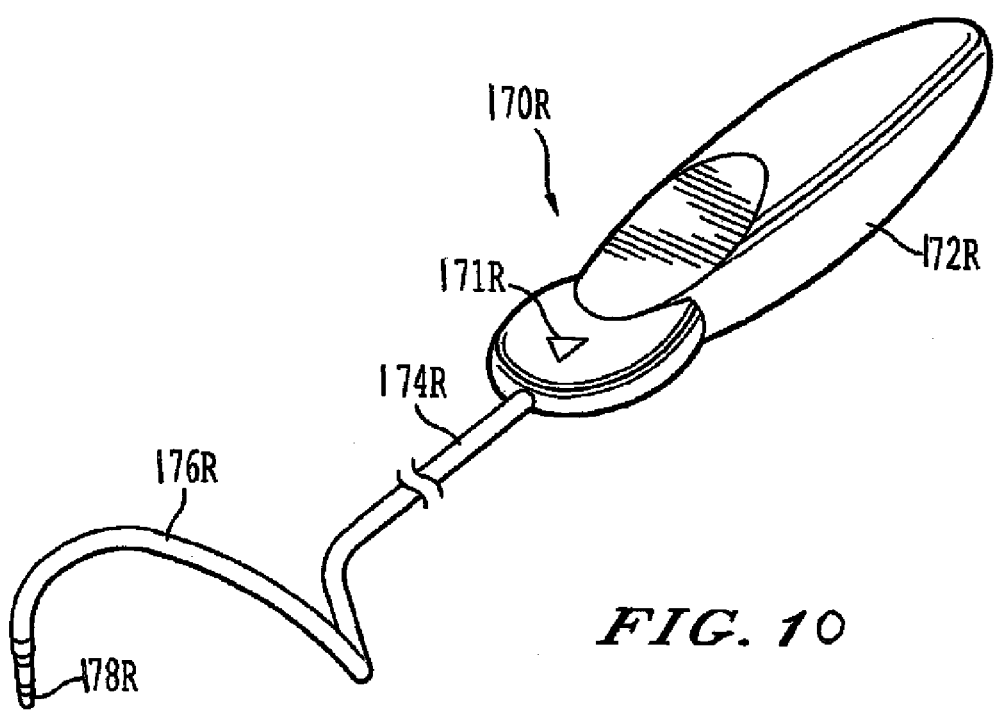

FIG. 10 illustrates an embodiment of right superior needle 70R of the present invention (left superior needle is a mirror image of the right superior needle). Right superior needle 170R includes indicia 171R, handle 172R, shaft 174R, curved portion 176R, and tip portion 178R. Indicia 171R designates whether the needle is the right or left needle by pointing to the surgeon's right or left side, as the surgeon holds the needle handle. (The surgeon's right side corresponds to the patient's left side.)

Figure 11:
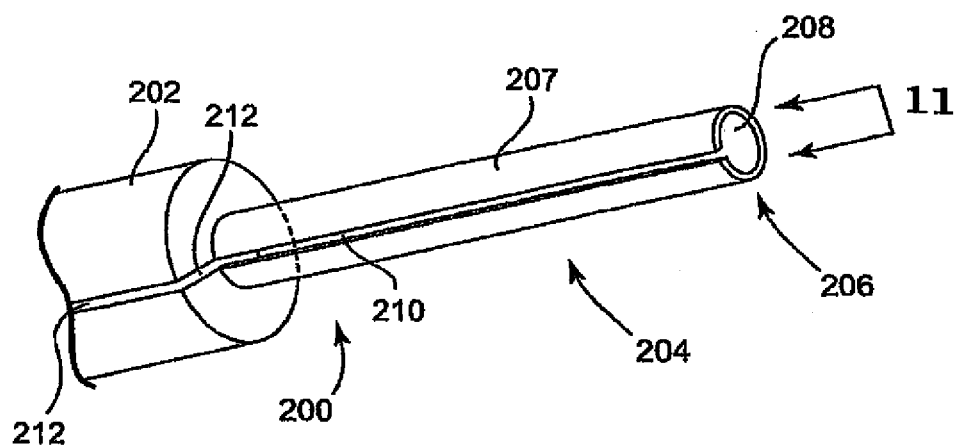

Referring to FIG. 11, delivery tool 200 includes handle 202 connected to hollow elongate inserter 204. Hollow elongate inserter 204 is an example of an inserter that can be used to insert an extension portion through tissue, with reduced contact between the extension portion and the tissue. For implant extensions that do not include a sheath or other removable covering (e.g., because the sheath can be difficult to remove in the absence of an external incision, as relates to exemplary methods of the present description) an insertion tool such as tool 200 can be used to reduce contact between implant and tissue, during implantation. Elongate hollow inserter 204 includes an elongate slotted tube 207 extending from handle 202 to distal end 206. An opening for inserting an implant extension portion, slot 210, extends along the length of tube 207, and also (optionally, and as illustrated) into handle 202 as slot 212. Internal bore 208 extends the length of tube 207 to form a hollow interior of tube 207 (bore 208). An extension portion of an implant can be inserted into slot 210 (and 212), to be contained by tube 207 within bore 208, for implantation. Tube 207 can act to encapsulate or otherwise protect the extension portion as the extension portion is pushed through tissue (using tool 200). Distal end 206 may be open (as illustrated), closed, or sized to receive a self-fixating tip. For example, distal end 206 can engage a self-fixating tip by contacting a complementary surface, optionally in a desired orientation. Once an extension portion is pushed into tissue of the patient, using tool 200, the extension portion can be removed from tool 200 by exiting tube 207 through slot 210. Tube 207 is shown to be straight, but may optionally be curved as desired to reach a desired tissue location. Optionally, another insertion tool such as an elongate needle may be placed within bore 208. The second tool may include an end that engages a self-fixating tip to push the tip through bore 208 and into tissue of the pelvic region. After the self-fixating tip is located within tissue as desired, the second tool may disengage the tip and be removed from bore 208 of tube 207, and tool 200 can be removed from the tissue path.

Figure 12:
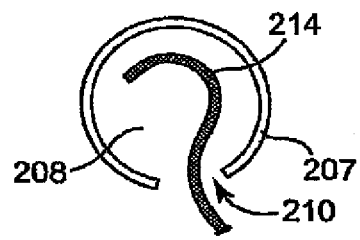

Referring now to FIG. 12, shown is an end, cross section view of elongate hollow inserter tool 200 looking in the direction from distal end 206 toward handle 202, FIG. 12 shows tool 200 from this end view, with implant 214 (e.g., mesh extension portion) shown partially within bore 208 and partially extending out through slot 210. FIG. 12 illustrates that a mesh strip (e.g., extension portion, also in an end cross-section view) may be inserted and removed from bore 218 through slot 210, prior to implanting a mesh strip (e.g., 214) into a tissue path; once the mesh strip is placed, tool 200 can be removed from the mesh strip also by passing the mesh strip (214) through slot 210. Optionally, a tool such as tool 200, designed to include a hollow interior for containing an extension portion of an implant, particularly useful for implanting an extension portion that does not include a protective sheath, can additionally include a cover that can open or close an elongate opening such as slot 210.

Implants of the invention can be implanted according to methods that include placement of a tissue support portion of an implant at a location to support pelvic tissue (e.g., periurethral tissue). One or more expansion members associated with the tissue support portion can expand in association with the periurethral tissue and stabilize the support portion, which can provide improved treatment for female urinary incontinence and vaginal prolapse. One or more extension portions are also placed anatomically to support the central support portion. For example, tissue fasteners can be present at distal ends of extension portions and can be placed at internal tissue of the pelvic region such as muscle, ligament, tendon, fascia, bone, etc. The length of an adjustable extension portion can be adjusted to adjust the position of the tissue support portion or to adjust the tension applied to the adjustable extension portion in supporting the tissue support portion.

Implantation can be accomplished through a medial incision such as transvaginally (for female anatomy), and by use of an insertion tool (e.g., any insertion tool described herein) that engages a distal end of the extension portion, such as by engaging a tissue fastener. Upon placement of the distal ends of extension portions, and the tissue support portion, the length of the extension portion may be reduced or lengthened by moving a segment of extension portion relative to a tensioning member, to adjust the position of the tissue support portion or the tension applied to the support portion.

For example, a tensioning member can be affixed to a proximal end of a distal part of an extension portion, and a (distal) segment of the proximal part of extension portion can extend through the tensioning member (in and out of the entry and exit apertures respectively). Adjustment can be performed by adjusting the amount (in terms of length) of the extension portion that extends through the tensioning member. The adjustment can be performed to provide a desired amount of tension between the central support portion and the distal end of the extension portion. In adjusting the implant, excess extension portion material (i.e., the extension portion material leading away from the tensioning member) can be trimmed away from the implant. The adjustment can be performed prior to insertion of the implant, during insertion of the implant, or after the implant has been inserted. In some methods, the mesh is transvaginally implanted, and the implant is adjusted and trimmed at the vaginal mucosa prior to any substantial tissue healing which may make portions of the mesh difficult to access.

Some tensioning members can provide one-way adjustability, while others can provide two-way adjustability. For one-way adjustability, the tensioning member can include a frictional element (such as teeth) to prevent the extension portion from moving through the tensioning member in an opposite direction. For two-way adjustability, the extension portion can move through the tensioning member in both directions, but then can be reconfigured to provide one-way adjustability.

Any of the above general and detailed descriptions of features of implants, insertion tools, tissue fasteners, and methods, etc., can be used in any desired combination, for treating female or male pelvic conditions.

Other embodiments of the invention are directed to systems and methods that uses a fiber-containing composition to form a reinforced implant. The reinforced implant can be used for the treatment of anterior or posterior vaginal repair. The system can include (a) an implant for the treatment of anterior or posterior vaginal repair; and (b) a composition comprising non-absorbable fibers of different sizes which can be applied to and set on all or a portion of the implant.

Any implant for the treatment of anterior or posterior vaginal repair can be used for reinforcement, including implants having the expansion member and tensioning member, as well as implants already known in the art, including those referenced herein.

The non-absorbable fibers of different sizes can be made from a material such as polypropylene fibers. Short cut polypropylene fibers are commercially available and can be included in the composition. Exemplary length ranges of short cut fibers are from about 1 mm to about 50 mm, or from about 3 mm to about 25 mm. Exemplary fiber sizes can are in the range of about 1 denier/filament to about 20 denier/filament. The fibers can be suspended in a setting composition that includes a biocompatible cement or sealant material such as a cyanoacrylate derivative (e.g., Histoacryl™ or Dermabond™).

In a related embodiment, the invention provides a method for promoting anterior or posterior vaginal repair. The method comprises steps of: (a) providing an implant for the treatment of anterior or posterior vaginal repair; (b) applying a composition comprising non-absorbable fibers of different sizes to all or a portion of the implant to form a reinforced implant; and (c) providing the reinforced implant at a pelvic tissue location to promote anterior or posterior vaginal repair.

The composition comprising non-absorbable fibers can be applied to the implant prior to, during, or after implantation. The applied fibers can provide an implant that better conforms to the patient's anatomy at the implantation site. The applied fibers can also reinforce the implant to provide additional support strength for treatment of anterior or posterior vaginal repair.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An implant configured to provide support to a urethra, the implant comprising a central support portion and one or more extension portion(s) from the central support portion, the central support portion comprising two opposed major surfaces having a thickness therebetween, a length dimension, and a width dimension, the extension portion(s) extending from the central support portion in the length dimension, wherein the central support portion comprises an expansion member configured to expand in the width dimension, the implant further comprising a tensioning member positioned along the extension portion, wherein the extension portion can be adjusted at the tensioning member to provide tensioning of the implant following implantation.

2. The implant of claim 1 wherein the expansion member comprises a resilient rigid material or material with a shape memory property.

3. The implant of claim 1 wherein the expansion member is integrated into, or attached to a material of the central support portion.

4. The implant of claim 1 wherein the expansion member is associated with a mesh structure of the central support portion, and is capable of expanding the mesh structure upon implantation of the implant.

5. The implant of claim 1 wherein the expansion member is elongate and in the form of a coil or a spring.

6. The implant of claim 1 wherein the expansion member is elongate and is arranged with a length oriented in a direction perpendicular to the length dimension.

7. The implant of claim 5 comprising two or more expansion members elongate and in the form of a coil or a spring, arranged perpendicular to a direction of extension of the implant, each positioned in the central support portion a distance from a centerline of the central support portion.

8. The implant of claim 1 wherein the expansion member comprises a biodegradable material.

9. The implant of claim 1 wherein the implant comprises two or more extension portions extending from the central support portion.

10. The implant of claim 9 wherein the two or more extension portions have ends configured to be attached to target pelvic tissue.

11. The implant of claim 10 wherein the ends each comprise a tissue anchoring member.

12. The implant of claim 1 wherein the central support portion, the extension portion(s), or both, comprise a mesh construction.

13. The implant of claim 12 wherein the mesh construction is a molded, non-woven construction.

14. The implant of claim 1 wherein the extension portion comprises a proximal extension portion and a distal extension portion, wherein the proximal extension portion is positioned between the central support portion and the distal extension portion, and the tensioning member connects the proximal extension portion to the distal extension portion.

15. The implant of claim 14 wherein, the tensioning member can allow adjustment of the length of the extension portion by allowing movement of material of the proximal extension portion, material of the distal extension portion, or both, through the tensioning member.

16. A system for the treatment of incontinence or prolapse, the system comprising:
(a) an implant configured to provide support to the urethra, the implant comprising a central support portion and one or more extension portion(s) from the central support portion, the central support portion comprising two opposed major surfaces having a thickness therebetween, a length dimension, and a width dimension, the extension portion(s) extending away from the central support portion in the length dimension, wherein the central support portion comprises an expansion member configured to expand in the width dimension, the implant further comprising a tensioning member positioned along the extension portion, wherein the extension portion can be adjusted in conjunction with the tensioning member to provide tensioning of the implant following implantation; and
(b) an implant delivery tool configured to deliver the implant and position the support portion of the implant in contact with periurethral tissue.

17. The system of claim 16 wherein the implant delivery tool comprises a hollow portion or bore in which a portion or all of the implant can be placed.

18. The system of claim 16 wherein at least a portion of the implant is loaded in the implant delivery tool to provide the expansion member in a compressed configuration.

19. A method for the treatment of incontinence or prolapse, the method comprising steps of:
(a) providing a system comprising an implant associated with an implant delivery tool, wherein the implant is configured to provide support to the urethra, the implant comprising a central support portion and one or more extension portion(s) extending from the central support portion, the central support portion comprising two opposed major surfaces having a thickness therebetween, a length dimension, and a width dimension, the extension portion(s) extending away from the central support portion in the length dimension, wherein the central support portion comprises an expansion member configured to expand in the width dimension, the implant further comprising a tensioning member positioned along the extension portion,
(b) delivering the implant into pelvic tissue to place the central support portion in contact with periurethral tissue;
(c) allowing expansion member to expand in contact with periurethral tissue; and
(d) adjusting the extension portion using the tensioning member to provide tensioning of the implant to provide treatment of incontinence or prolapse.

20. The method of claim 19, wherein the extension portion is adjusted at vaginal mucosa following implantation.

21. The implant of claim 1, comprising an anchor at a distal end of the extension portion.

22. The implant of claim 1 wherein the implant is configured for transvaginal insertion.

23. The system of claim 16 wherein the implant is configured for transvaginal insertion and the implant delivery tool is configured to transvaginally deliver the implant.

24. The method of claim 19 wherein delivering the implant comprises delivering the implant transvaginally.

* * * * *